US012564518B2

(12) United States Patent
Bor

(10) Patent No.: US 12,564,518 B2
(45) Date of Patent: Mar. 3, 2026

(54) PERFORMING LASER VITREOLYSIS ON AN EYE WITH AN INTRAOCULAR LENS

(71) Applicant: Alcon Inc., Fribourg (CH)

(72) Inventor: Zsolt Bor, San Clemente, CA (US)

(73) Assignee: Alcon Inc., Fribourg (CH)

( * ) Notice: Subject to any disclaimer, the term of this patent is extended or adjusted under 35 U.S.C. 154(b) by 730 days.

(21) Appl. No.: 17/938,587

(22) Filed: Oct. 6, 2022

(65) Prior Publication Data

US 2023/0157887 A1 May 25, 2023

Related U.S. Application Data

(60) Provisional application No. 63/281,514, filed on Nov. 19, 2021.

(51) Int. Cl.
*A61F 9/008* (2006.01)
*G02B 26/06* (2006.01)

(52) U.S. Cl.
CPC .......... *A61F 9/00834* (2013.01); *G02B 26/06* (2013.01); *A61F 2009/0087* (2013.01)

(58) Field of Classification Search
CPC .......... A61F 9/00834; A61F 2009/0087; A61F 9/00825; A61F 2009/00874; G02B 26/06
See application file for complete search history.

(56) References Cited

U.S. PATENT DOCUMENTS

| | | |
|---|---|---|
| 3,780,979 A | 12/1973 | De Guillebon |
| 4,357,088 A | 11/1982 | Pomerantzeff |

| | | |
|---|---|---|
| 5,312,396 A | 5/1994 | Feld |
| 5,909,270 A | 6/1999 | Moser |
| 6,142,630 A | 11/2000 | Koester |
| 6,322,556 B1 | 11/2001 | Gwon |
| 6,789,900 B2 | 9/2004 | Van De Velde |
| 7,374,287 B2 | 5/2008 | Van De Velde |

(Continued)

FOREIGN PATENT DOCUMENTS

| | | |
|---|---|---|
| AU | 2018274939 B2 | 6/2020 |
| CN | 210009227 U | 2/2020 |

(Continued)

OTHER PUBLICATIONS

Blake F. Webb, et al.; "Prevalence of vitreous floaters in a community sample of smartphone users"; Internat'l Journal of Ophthalmology; Jun. 18, 2013; pp. 402-405; 6(3); PMC/ US National Library of Medicine National Institutes of Health.

(Continued)

*Primary Examiner* — Carl H Layno
*Assistant Examiner* — Aya Ziad Bakkar
(74) *Attorney, Agent, or Firm* — Patterson + Sheridan, LLP

(57) ABSTRACT

In certain embodiments, an ophthalmic laser system includes a laser device and a computer, where the laser device includes a laser and a phase modulator. The laser device directs a laser beam towards a target in an eye, where an intraocular lens (IOL) is disposed within the eye. The IOL has a phase profile that yields an IOL phase shift of light entering the eye. The laser generates the laser beam. The phase modulator has a phase front that yields a first phase shift of the laser beam that changes to a second phase shift when the laser beam reaches the IOL. The second phase shift is an inverse to the IOL phase shift.

20 Claims, 3 Drawing Sheets

(56) References Cited

U.S. PATENT DOCUMENTS

| | | |
|---|---|---|
| 7,510,282 B2 | 3/2009 | Ueno |
| 7,520,613 B2 | 4/2009 | Saito et al. |
| 7,703,922 B2 | 4/2010 | Van De Velde |
| 8,480,659 B2 | 7/2013 | Frey et al. |
| 8,652,602 B1 | 2/2014 | Dolla |
| 8,783,868 B2 | 7/2014 | Qiu |
| 8,876,808 B2 | 11/2014 | Feklistov et al. |
| 8,994,753 B2 | 3/2015 | Nakano |
| 9,033,500 B2 | 5/2015 | Utsunomiya |
| 9,603,519 B2 | 3/2017 | Bor et al. |
| 9,675,243 B2 | 6/2017 | Sasak et al. |
| 9,789,002 B2 | 10/2017 | Van De Velde |
| 10,130,511 B2 | 11/2018 | Dantus |
| 10,478,342 B2 | 11/2019 | Dick |
| 10,555,835 B2 | 2/2020 | Schuele et al. |
| 2007/0258094 A1 | 11/2007 | Izatt et al. |
| 2007/0291277 A1 | 12/2007 | Everett |
| 2009/0073384 A1 | 3/2009 | Warden |
| 2009/0137989 A1 | 5/2009 | Kataoka |
| 2009/0196477 A1 | 8/2009 | Cense et al. |
| 2010/0123873 A1 | 5/2010 | Raymond |
| 2010/0152847 A1 | 6/2010 | Padrick |
| 2011/0077557 A1 | 3/2011 | Wing et al. |
| 2012/0281235 A1 | 11/2012 | Murata |
| 2013/0131652 A1 | 5/2013 | Dick |
| 2013/0173029 A1 | 7/2013 | Caldeira et al. |
| 2014/0058367 A1 | 2/2014 | Dantus |
| 2014/0216468 A1 | 8/2014 | Goldshleger |
| 2014/0257257 A1 | 9/2014 | Grant et al. |
| 2014/0268036 A1 | 9/2014 | Ketterling et al. |
| 2014/0276674 A1 | 9/2014 | Lee |
| 2015/0190278 A1 | 7/2015 | Gooding |
| 2015/0342782 A1 | 12/2015 | Mordaunt |
| 2016/0058617 A1 | 3/2016 | Luttrull et al. |
| 2016/0074214 A1 | 3/2016 | Palanker et al. |
| 2016/0074221 A1 | 3/2016 | Tassignon et al. |
| 2016/0166431 A1 | 6/2016 | Vogler et al. |
| 2016/0227999 A1 | 8/2016 | An et al. |
| 2016/0235588 A1 | 8/2016 | Hart et al. |
| 2016/0256324 A1 | 9/2016 | Suzuki |
| 2016/0278629 A1 | 9/2016 | Schuele |
| 2016/0302969 A1 | 10/2016 | Yamamoto |
| 2017/0181625 A1 | 6/2017 | Kawakami et al. |
| 2017/0252213 A1 | 9/2017 | Furuuchi et al. |
| 2017/0326003 A1 | 11/2017 | Schuele et al. |
| 2018/0028354 A1 | 2/2018 | Heeren |
| 2018/0028355 A1 | 2/2018 | Raksi |
| 2018/0140257 A1 | 5/2018 | Govindjee et al. |
| 2018/0206719 A1 | 7/2018 | Adler et al. |
| 2018/0317767 A1 | 11/2018 | Ryan |
| 2018/0353064 A1 | 12/2018 | Soetikno et al. |
| 2018/0368915 A1 | 12/2018 | Xia et al. |
| 2019/0159933 A1 | 5/2019 | Romano et al. |
| 2019/0282403 A1 | 9/2019 | Barrett et al. |
| 2019/0290124 A1 | 9/2019 | Laforest et al. |
| 2019/0313903 A1 | 10/2019 | Mckinnon |
| 2019/0365569 A1 | 12/2019 | Skovgaard et al. |
| 2020/0038241 A1 | 2/2020 | Wang et al. |
| 2020/0060873 A1 | 2/2020 | Heeren |
| 2020/0085292 A1 | 3/2020 | Fukuma et al. |
| 2020/0129336 A1 | 4/2020 | Schuele et al. |
| 2020/0130103 A1 | 4/2020 | Choi |
| 2020/0192080 A1 | 6/2020 | Karam |
| 2020/0196853 A1 | 6/2020 | Van Hemert et al. |
| 2020/0273218 A1 | 8/2020 | Camino et al. |
| 2020/0397289 A1 | 12/2020 | Ralston |
| 2020/0400422 A1 | 12/2020 | Ralston |
| 2021/0100450 A1 | 4/2021 | Amma et al. |
| 2021/0186753 A1 * | 6/2021 | Al-Qaisi ............. A61F 9/00736 |
| 2021/0275009 A1 | 9/2021 | Yates |
| 2021/0378507 A1 | 12/2021 | Wallace et al. |
| 2021/0386586 A1 | 12/2021 | Bor |
| 2022/0012459 A1 | 1/2022 | Schwiegerling |
| 2022/0031511 A1 | 2/2022 | Charles |
| 2023/0157889 A1 | 5/2023 | Bor |

FOREIGN PATENT DOCUMENTS

| | | | |
|---|---|---|---|
| CN | 108371542 B | 4/2020 | |
| CN | 109196333 B | 12/2020 | |
| CN | 111281651 B | 12/2020 | |
| CN | 112862782 A | 5/2021 | |
| CN | 112587302 B | 6/2021 | |
| CN | 112587304 B | 6/2021 | |
| DE | 19705044 A1 | 8/1998 | |
| DE | 102019007147 A1 | 4/2021 | |
| DE | 102019007148 A1 | 4/2021 | |
| EP | 0770370 A2 | 2/1997 | |
| EP | 1212022 B1 | 3/2005 | |
| EP | 1563785 A1 | 8/2005 | |
| EP | 1638452 B1 | 10/2006 | |
| EP | 1838212 A1 | 10/2007 | |
| EP | 2144552 A1 | 1/2010 | |
| EP | 1928297 B1 | 11/2010 | |
| EP | 2459138 A2 | 6/2012 | |
| EP | 2525706 A2 | 11/2012 | |
| EP | 2898820 A1 | 7/2015 | |
| EP | 3061429 A1 | 8/2016 | |
| EP | 2890340 B1 | 2/2017 | |
| EP | 3459487 A1 | 3/2019 | |
| EP | 3501463 A1 | 6/2019 | |
| EP | 3636137 A1 | 4/2020 | |
| EP | 3861924 A1 | 8/2021 | |
| GB | 2469249 A | 10/2010 | |
| JP | 5767014 B2 | 6/2015 | |
| JP | 2017176558 A | 10/2017 | |
| JP | 6410468 B2 | 10/2018 | |
| JP | 2018196821 A | 12/2018 | |
| JP | 2018196822 A | 12/2018 | |
| JP | 2020022569 A | 2/2020 | |
| JP | 6736304 B2 | 7/2020 | |
| JP | 6839902 B2 | 2/2021 | |
| RU | 2661016 C1 | 7/2018 | |
| RU | 2692666 C1 | 6/2019 | |
| RU | 2695629 C1 | 7/2019 | |
| RU | 2710058 C2 | 12/2019 | |
| RU | 2726468 C1 | 7/2020 | |
| WO | 9958047 A1 | 11/1999 | |
| WO | 0137769 A1 | 5/2001 | |
| WO | 0195791 A1 | 12/2001 | |
| WO | 2007059189 A2 | 5/2007 | |
| WO | 2009033110 A2 | 3/2009 | |
| WO | 2009036104 A2 | 3/2009 | |
| WO | 2009039315 A2 | 3/2009 | |
| WO | 2009059400 A1 | 5/2009 | |
| WO | 2010117386 A1 | 10/2010 | |
| WO | 2014053824 A1 | 4/2014 | |
| WO | 2015131135 A1 | 9/2015 | |
| WO | 2015171793 A1 | 11/2015 | |
| WO | 2016033590 A1 | 3/2016 | |
| WO | 2017062673 A1 | 4/2017 | |
| WO | 2017196306 A1 | 11/2017 | |
| WO | 2017205857 A1 | 11/2017 | |
| WO | 2020074532 A1 | 4/2020 | |
| WO | 2020180729 A1 | 9/2020 | |
| WO | 2020215359 A1 | 10/2020 | |
| WO | 2020216763 A1 | 10/2020 | |
| WO | 2020257711 A1 | 12/2020 | |
| WO | 2021023799 A1 | 2/2021 | |
| WO | 2021049243 A1 | 3/2021 | |
| WO | 2021066047 A1 | 4/2021 | |
| WO | WO-2021069168 A1 * | 4/2021 | ............. A61F 9/008 |
| WO | 2021092211 A1 | 5/2021 | |
| WO | 2021183637 A1 | 9/2021 | |
| WO | 2022149028 A1 | 7/2022 | |
| WO | 2023089416 A1 | 5/2023 | |
| WO | 2023089459 A1 | 5/2023 | |
| WO | 2023097391 A1 | 6/2023 | |

OTHER PUBLICATIONS

Chirag P. Shah, et al., YAG Laser Vitreolysis vs Sham YAG Vitreolysis for Symptomatic Vitreous Floaters A Randomized Clinical Trial, JAMA Ophthalmology, Sep. 2017, 918-923, 135-9.

US 12,564,518 B2

Page 3

(56) References Cited

OTHER PUBLICATIONS

ELLEX Website, Treatment Guidelines—Laser Floater Removal; 2016, Ellex Medical Pty Ltd. E&OE. VB0002E, downloaded Apr. 20, 2017.
Felix Sauvage et al: "Photoablation of Human Vitreous Opacities by Light—Induced Vapor Nanobubbles", ACS Nano, vol. 13, No. 7, Jul. 9, 2019, pp. 8401-8416.
Kim Jihwan et al. "Nonmechanical Laser Beam Steering Based on Polymer Polarization Gratings: Design Optimization and Demonstration", Journal of Lightwave Technology, vol. 33, No. 10, pp. 2068-2077, May 15, 2015.
Michael J. Escuti, et al., "Geometric-Phase Holograms", Optics & Photonics News, pp. 22-29, Feb. 2016.
Milston Rebecca et al: "Vitreous floaters: Etiology, diagnostics, and management", Survey of Ophthalmology, vol. 61, No. 2, Mar. 1, 2016, pp. 211-227.
Nicusor Iftimia et al: "Hybrid retinal imaginer using line-scanning laser ophthalmoscopy and spectral domain optical coherence tomography", Optics Express, vol. 14, No. 26, Dec. 22, 2006.
Reece Bergstrom, et al., Vitreous Floaters, National Center for Biotechnology Information, May 21, 2020, 4 pages, Bookshelf ID NBK470420, StatPearls Publishing LLC, online.
Wikipedia Encyclopedia, Floater, Wikipedia Encyclopedia, Mar. 29, 2021, online: https://en.wikipedia.org/wiki/rloater?wprov=sfti 1.
Zhang Yunbo et al: "Parallel large-range scanning confocal microscope based on a digital micromirror device", Optik vol. 124, No. 13 (2013), Aug. 4, 2012, pp. 1585-1588.
Damodaran et al., "Digital micromirror device based ophthalmoscope with concentric circle scanning", 2017, pp. 2766-2780, vol. 8, No. 5, Biomedical Optics Express.
Fischer et al., "Scanning Laser Ophthalmoscopy (SLO)", In: Bille JF, editor. High Resolution Imaging in Microscopy and Ophthalmology: New Frontiers in Biomedical Optics [Internet], Aug. 14, 2019, accessed on Jan. 30, 2023 from https://www.ncbi.nlm.nih.gov/books/NBK554043, Springer.
Ginner et al., "Wide-Field OCT Angiography at 400 KHz Utilizing Spectral Splitting", Photonics, Oct. 23, 2014, pp. 369-379, vol. 1, No. 4.
Heidelberg Engineering GMBH, "Spectralis. Hardware Operating Instructions," Version 001, Aug. 2007.
Heidelberg Engineering, "SPECTRALIS. Multimodal Imaging Platform Optimized for the Posterior Segment", accessed on Jan. 30, 2023 from https://business-lounge.heidelbergengineering.com/us/en/products/spectralis/spectralis/.
Hofer et al., "Dispersion encoded full range frequency domain optical coherence tomography", Jan. 5, 2009, pp. 7-24, vol. 17, No. 1, Optics Express, US.
Hofer et al., "Fast dispersion encoded full range optical coherence tomography for retinal imaging at 800 nm and 1060 nm", Mar. 1, 2010, pp. 4898-4919, vol. 18, No. 5, Optics Express.
Leitgeb et al., "Complex ambiguity-free Fourier domain optical coherence tomography through transverse scanning", 2007, pp. 3453-3455, vol. 32, Optics Letters.
Li et al., "DMD-based three-dimensional chromatic confocal microscopy", 2020, pp. 4349-4356, vol. 59, No. 14, Applied Optics.
Martial et al., "Programmable Illumination and High-Speed, Multi-Wavelength, Confocal Microscopy Using a Digital Micromirror", Aug. 2012, e43942, vol. 7, No. 8, PLOS ONE.
Reznicek Lukas et al., "Wide-Field Megahertz OCT Imaging of Patients with Diabetic Retinopathy", Journal of Diabetes Research, 2015, 5 pages.
Ruggeri et al., "Imaging and full-length biometry of the eye during accommodation using spectral domain OCT with an optical switch", Jul. 1, 2012, pp. 1506-1520, vol. 3, No. 7, Biomedical Optics Express.
Sarunic et al., "Instantaneous complex conjugate resolved spectral domain and swept-source OCT using 3×3 fiber couplers", Feb. 2005, pp. 957-967, vol. 13, No. 3, Optics Express.
Shields et al., "Wide-angle Imaging of the Ocular Fundus", Review of the Ophthalmology, Feb. 15, 2003.

Singh, "Lasers Take Aim at Floaters", Ophthalmology Management, Jul. 1, 2019, pp. 38, 40-42, 59, vol. 23.
Singh, "Modern vitreolysis—YAG laser treatment now a real solution for the treatment of symptomatic floaters", Survey of Ophthalmology, Mar. 3, 2020, pp. 581-591, vol. 65, No. 5.
SunLED, NanoPoint-0201 Series LEDs, published Feb. 15, 2016, www.SunLEDusa.com.
Volk Optical, "Volk Idrees Mid-Vitreous Lens", Dec. 20, 2020, accessed on Dec. 20, 2020 from https://www.volk.com/...s?pr_prod_strat=collection_fallback&pr_rec_pid=4513049018402&pr_ref_pid=4513048952866&pr_seq=uniform.
Volk Optical, "Volk Singh Mid-Vitreous Lens", Dec. 20, 2020, accessed on Dec. 20, 2020 from https://www.volk.com/products/singh-mid-vitreous-vitreous-slit-lamp-lens?_pos=3&amp;amp;_sid=b50c0674f&amp;amp;_ss=r.
Wang et al., "In vivo full range complex Fourier domain optical coherence tomography", Jan. 30, 2007, 054103, vol. 90, Applied Physics Letters.
Wojtkowski et al., "Full range complex spectral optical coherence tomography technique in eye imaging", 2002, pp. 1415-1417, vol. 27, No. 16, Optics Letters.
Yasuno et al., "Simultaneous B—M-mode scanning method for real-time full-range Fourier domain optical coherence tomography", 2006, pp. 1861-1865, vol. 45, No. 8, Applied Optics.
Zhang et al., Removal of a mirror image and enhancement of the signal-to-noise ratio in Fourier-domain optical coherence tomography using an electro-optic phase modulator, Jan. 15, 2005, vol. 30, No. 2, Optics Letters.
Zhou et al., "Dual channel dual focus optical coherence tomography for imaging accommodation of the eye", May 25, 2009, pp. 8947-8955, vol. 17, No. 11, Optics Express.
Adrian G.H. Podoleanu et al., Combined optical coherence tomograph and scanning laser ophthalmoscope mi nije dostupan besplatno., Electronics Letters, 34 (11), 1998.
Chi-Hung Lee, et al., Imaging vitreous floaters and cataracts with optical simulations, Optik, 194, 1-9, 2019.
Christy K. Sheehy et al., High-speed, image-based eye tracking with a scanning laser ophthalmoscope, Biomedical Optics Express, vol. 3, No. 10, 2012.
D. H. Kelly, "Retinal Inhomogeneity. II. Spatial Summation," J. Opt. Soc. Am., pp. 114-119, vol. 1, No. 1 (Jan. 1984).
D. H. Kelly, "Retinal Inhomogeneity. III. Circular-Retina Theory," D.H. Kelly, J. Opt. Soc. Am., pp. 810-819, vol. 2, No. 6 (Jun. 1985).
D.H. Kelly, "Visual Processing of Moving Stimuli," J. Opt. Soc. Am., pp. 216-225, vol. 2, No. 2 (Feb. 1985).
D.H. Kelly,, "Motion and Vision. II. Stabilized Spatio-Temporal Threshold Surface," J. Opt. Soc. Am., pp. 1340-1349, vol. 69, No. 10 (Oct. 1979).
D.H.Kelly, "Retinal Inhomogeneity. I. Spatiotemporal Contrast Sensitivity," J. Opt. Sec. Am., pp. 107-113, vol. 1, No. 1 (Jan. 1984).
Mojana F. et al.. Observations by spectral-domain optical coherence tomography combined with simultaneous scanning laser ophthalmoscopy: imaging of the vitreous, American Journal of Ophthalmol. Apr. 2010;149(4):641-650.
Nidek, Scanning Laser Ophthalmoscope Mirante SLO/OCT Mirante SLO, https://www.nidek-intl.com/product/ophthaloptom/diagnostic/dia_retina/mirante.htm.
Peter G. J. Barten, "Contrast Sensitivity of the Human Eye and its Effects on Image Quality," Chapter 3, pp. 27-40, Model for the spatial contrast sensitivity of the eye, (1999).
Pointer, J. S., & Hess, R. F. "The contrast sensitivity gradient across the human visual field: With emphasis on the low spatial frequency range,", R. F. Vision Research, 29(9), 1133-1151 (1989).
Sebag J et al., Vitreous and Vitreoretinal Interface, Ch. 21, 2015.
Sebag J., Vitreous and Vision Degrading Myodesopsia. Progress in Retinal and Eye Research Nov. 2020;79.
T Ivanova et al, Vitrectomy for primary symptomatic vitreous opacities: an evidence-based review, Eye (Lond) May 2016;30(5):645-55.
Teri T Kleinberg et al., Vitreous substitutes: a comprehensive review, Survey of Ophthalmology, 56 (4), 2011.

* cited by examiner

PERFORMING LASER VITREOLYSIS ON AN EYE WITH AN INTRAOCULAR LENS

TECHNICAL FIELD

The present disclosure relates generally to ophthalmic laser surgical systems, and more particularly to performing laser vitreolysis on an eye with an intraocular lens.

BACKGROUND

In ophthalmic laser surgery, a surgeon may direct a laser beam into an eye to treat the eye. For example, in laser vitreolysis, a laser beam is directed into the vitreous to disintegrate eye floaters. Eye floaters are clumps of collagen proteins that form in the vitreous. These clumps disturb vision with moving shadows and distortions. The laser beam may be used to remove the floaters, thus improving vision.

BRIEF SUMMARY

In certain embodiments, an ophthalmic laser system includes a laser device and a computer, where the laser device includes a laser and a phase modulator. The laser device directs a laser beam towards a target in an eye, where an intraocular lens (IOL) is disposed within the eye. The IOL has a phase profile that yields an IOL phase shift of light entering the eye. The laser generates the laser beam. The phase modulator has a phase front that yields a first phase shift of the laser beam that changes to a second phase shift when the laser beam reaches the IOL. The second phase shift is an inverse to the IOL phase shift.

Embodiments may include none, one, some, or all of the following features:

The target comprising an eye floater.

The phase modulator comprises a diffractive optical element or a spatial light modulator. The computer may program the spatial light modulator to yield the first phase shift.

The computer determines the IOL phase shift, calculates the second phase shift as an inverse of the IOL phase shift, and calculates the first phase shift from the second phase shift. The computer may determine the IOL phase shift by measuring the phase shift of the IOL. The computer may calculate the first phase shift from the second phase shift by determining how the first phase shift changes between the phase modulator and the IOL according to wavefront propagation theory.

The ophthalmic laser system includes an ophthalmic microscope that gathers light reflected from within the eye to yield an image of the eye. The ophthalmic microscope may be, e.g., a slit lamp.

In certain embodiments, a method for performing laser vitreolysis includes instructing, by a computer, a laser device to direct a laser beam towards a target in an eye. An intraocular lens (IOL) is disposed within the eye and has a phase profile that yields an IOL phase shift of light entering the eye. The laser device includes a laser and a phase modulator. The phase modulator has a phase front that yields a first phase shift of the laser beam that changes to a second phase shift when the laser beam reaches the IOL, where the second phase shift is an inverse to the IOL phase shift. The laser beam is generated by the laser. The laser beam is modulated by the phase modulator to yield the first phase shift of the laser beam. The laser beam is directed by the laser device towards the target in the eye.

Embodiments may include none, one, some, or all of the following features:

The target comprising an eye floater.

The phase modulator comprises a diffractive optical element or a spatial light modulator. The computer may program the spatial light modulator to yield the first phase shift.

The method further includes: determining, by the computer, the IOL phase shift; calculating, by the computer, the second phase shift as an inverse of the IOL phase shift; and calculating, by the computer, the first phase shift from the second phase shift. The computer may determine the IOL phase shift by measuring a phase shift of the IOL. The computer may calculate the first phase shift from the second phase shift by determining how the first phase shift changes between the phase modulator and the IOL according to wavefront propagation theory.

The method further includes gathering, by an ophthalmic microscope, light reflected from within the eye to yield an image of the eye. The ophthalmic microscope may be a slit lamp.

DESCRIPTION OF EXAMPLE EMBODIMENTS

Figure 1:
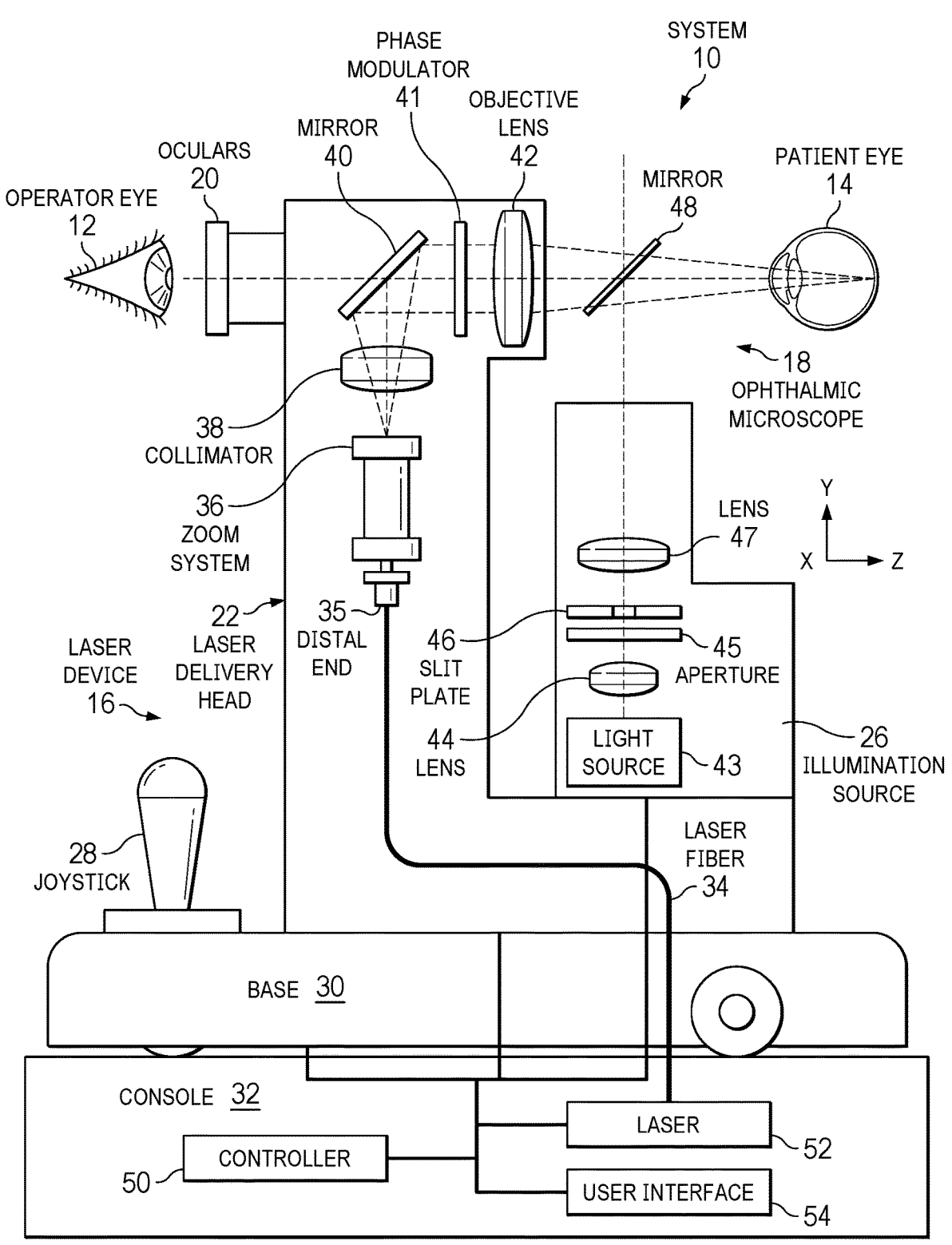
FIG. 1 illustrates an example of an ophthalmic laser system that an operator may use to perform laser vitreolysis on a patient eye to remove vitreous floaters, according to certain embodiments.

Referring now to the description and drawings, example embodiments of the disclosed apparatuses, systems, and methods are shown in detail. The description and drawings are not intended to be exhaustive or otherwise limit the claims to the specific embodiments shown in the drawings and disclosed in the description. Although the drawings represent possible embodiments, the drawings are not necessarily to scale and certain features may be simplified, exaggerated, removed, or partially sectioned to better illustrate the embodiments.

Some laser vitreolysis patients have a multifocal intraocular lens (IOL) implanted into their eye. A multifocal IOL adds a phase shift that diffracts incoming light to different focal points along the axis of the eye, allowing the patient to see objects at different distances. However, the IOL also diffracts a laser beam used to treat floaters to different focal points. Moreover, the laser beam may have a wavelength that causes the IOL to create even more focal points. That is, the IOL disperses and reduces laser energy at the floater, and may even cause laser energy to reach the retina.

Accordingly, the systems described herein add a phase profile to the laser beam that compensates for the phase shift caused by the IOL. For example, the systems include a phase modulator that adds a phase profile F1 to the laser beam. The laser beam enters the eye and the phase front changes to phase front F2, which is designed to be the inverse of the phase shift F3 generated by the IOL. As the laser beam passes through the IOL, phase shift F3 compensates for the phase shift F2, such that the IOL behaves as a monofocal lens with only one focus.

FIG. 1 illustrates an example of an ophthalmic laser system 10 that an operator (with an operator eye 12) may use to perform laser vitreolysis on a patient eye 14 to remove vitreous floaters, according to certain embodiments. Ophthalmic laser system 10 allows the operator to see floaters in relation to the retina and lens of the eye, and then direct a laser beam to break up the floaters. In the illustrated example, patient eye 14 has an axis (visual or optical) that defines a z-axis. The z-axis defines an x-axis and a y-axis orthogonal to the z-axis. In turn, the x-axis and the y-axis define an xy-plane. In the example, patient eye 14 includes a multifocal IOL (not shown). Examples of multifocal IOLs include diffractive and/or refractive multifocal, extended depth of focus, presbyopic, light adjustable multifocal, or other IOL.

In this document, inverse phase shifts have the same magnitude but are opposite in sign. For example, a +x phase shift is the inverse of a –x phase shift. Also in this document, the phase shifts of the IOL and the treatment laser are inverse at the wavelength of the treatment laser. For example, a multifocal IOL is typically designed to yield a phase shift at the wavelength of maximal retinal sensitivity. However, in this document, the phase shifts of the IOL and the treatment laser are inverse (i.e., equal in magnitude but of different signs) at the wavelength of the treatment laser.

In the example, ophthalmic laser system 10 comprises oculars 20, a laser delivery head 22, a slit illumination source 26, a positioning device (such as a joystick 28), a base 30, and a console 32, coupled as shown. Laser delivery head 22 includes a laser fiber 34, a distal end 35, a zoom system 36, a collimator 38, a mirror 40, a phase modulator 41, and an objective lens 42, coupled as shown. Slit illumination source 26 includes a light source 43, condenser lens 44, a variable aperture 45, a variable slit plate 46, a projection lens 47, and a mirror 48. Console 32 includes a computer (such as a controller 50), a laser 52, and a user interface 54, coupled as shown.

As an overview, ophthalmic laser system 10 includes a laser device 16 (e.g., laser 52, laser fiber 34, and laser delivery head 22) and an ophthalmic microscope 18 such as a slit lamp (e.g., oculars 20, objective lens 42, mirror 48, and slit illumination source 26). Operator eye 12 utilizes the optical path from oculars 20 through mirror 40, phase modulator 41, objective lens 42, and mirror 48 to view patient eye 14. A laser beam follows the laser path from laser 52 through laser delivery head 22 and mirror 48 to treat patient eye 14. In other embodiments, system 10 includes any suitable treatment system with a laser device, any suitable imaging system, and any suitable computer.

According to the overview, laser device 16 directs a laser beam towards a target in an eye. The eye has an intraocular lens (IOL) having a phase profile configured to yield an IOL phase shift of the laser beam. Laser 52 generates the laser beam. Phase modulator 41 has a phase front that yields a first phase shift of the laser beam that changes to a second phase shift when the laser beam reaches the IOL, where the second phase shift is the inverse to the IOL phase shift. As the laser beam passes through the IOL, the IOL phase shift compensates for the second phase shift, such that the IOL behaves as a monofocal lens with only one focus.

In more detail, in certain embodiments, oculars 20 allow operator eye 12 to view patient eye 14. Laser delivery head 22 delivers a laser beam of laser pulses from laser 52 of console 32 to patient eye 14. Laser fiber 34 of delivery head 22 transports the laser beam from laser 52 to the end of fiber 34. Zoom system 36 includes optical elements that change the spot size of the laser beam that exits fiber 34. Collimator 38 collimates the laser beam, and mirror 40 directs the beam to phase modulator 41.

Phase modulator 41 adds phase shift F1 to the laser beam to yield a phase profile F1. Phase modulator 41 may comprise, e.g., a diffractive optical element (such as one embodied in a glass plate) or a spatial light modulator (such as a programmable diffractive optical element). Phase modulator 41 may be instructed by controller to add the phase shift F1. In certain embodiments, controller 50 may instruct phase modulator 41 to adjust to a particular phase shift F1, depending on the IOL phase shift F3 of the IOL in the patient eye.

Objective lens 42 focuses the beam. Zoom system 36 and collimator 38 are configured to direct a parallel laser beam to mirror 40, in order to focus the laser beam onto the image plane of ophthalmic microscope 18. Mirror 40 may be a dichroic mirror that is reflective for the laser beam wavelength and transmissive for visible light.

Slit illumination source 26 of laser system 10 provides light that illuminates the surgical site of patient eye 14. Slit illumination source 26 includes light source 43, which emits light such as a high-intensity illumination light. Condenser lens 44 directs the light towards variable aperture 45 and variable slit plate 46. Variable aperture 45 defines the height of the light in the y-direction, and variable slit plate 43 defines the width of the light in the x-direction to form the light into a slit shape. Projection lens 47 directions the light towards prism mirror 48, which directs the slit of light into patient eye 14.

Base 30 supports laser delivery head 22 and slit illumination source 26. Joystick 28 moves base 30 in the x-, y-, and z-directions. Console 32 includes components that support the operation of system 10. Controller 50 of console 32 controls of the operation of components of system 10, e.g., base 30, laser delivery head 22, slit illumination source 26, laser 52, and/or user interface 54. Laser 52 supplies the laser beam. Any suitable laser 30 may be used, e.g., a femtosecond or nanosecond laser (e.g., Q-switched) with any suitable crystal (e.g., Nd:YAG, Erbium:YAG, Ti:Sapphire, or ruby). The laser beam may have any suitable wavelength, e.g., in a range from 500 nm to 1100 nm. User interface 54 communicates information between the operator and system 10.

Controller 50 controls the operation of system 10. In certain embodiments, controller 50 instructs phase modulator 41 to apply the first phase shift F1 to the laser beam. In addition, in certain embodiments, controller 50 calculates the phase shift F1. In the embodiments, controller 50 determines the IOL phase shift F3, calculates the second phase shift F2 as an inverse of the IOL phase shift F3, and calculates the first phase shift F1 from the second phase shift F2.

In certain cases, the IOL phase shift may be provided by the manufacturer. In other cases, controller 50 determines the IOL phase shift F3 by measuring the phase shift of the IOL. For example, controller 50 may use any of the following to measure the IOL phase shift: contact profilometer, confocal microscope, white light interferometer, optical aberrometer, interferometer, confocal chromatic microscope, atomic force microscope, etc. In certain embodiments, closed-loop adaptive optics can be used to measure phase shift F3. In the embodiments, a detector (such as a two-photon fluorescence detector) detects light reflected from the eye as the adaptive optics are adjusted and is used to determine when the optics are properly adjusted, which provides the measurement of phase shift F3.

In the embodiments, controller 50 calculates the second phase shift F2 as an inverse of the IOL phase shift F3. Controller 50 then calculates the first phase shift F1 from the second phase shift F2 by determining how the first phase shift F1 changes between phase modulator 41 and the IOL according to wavefront propagation theory.

Figure 2:
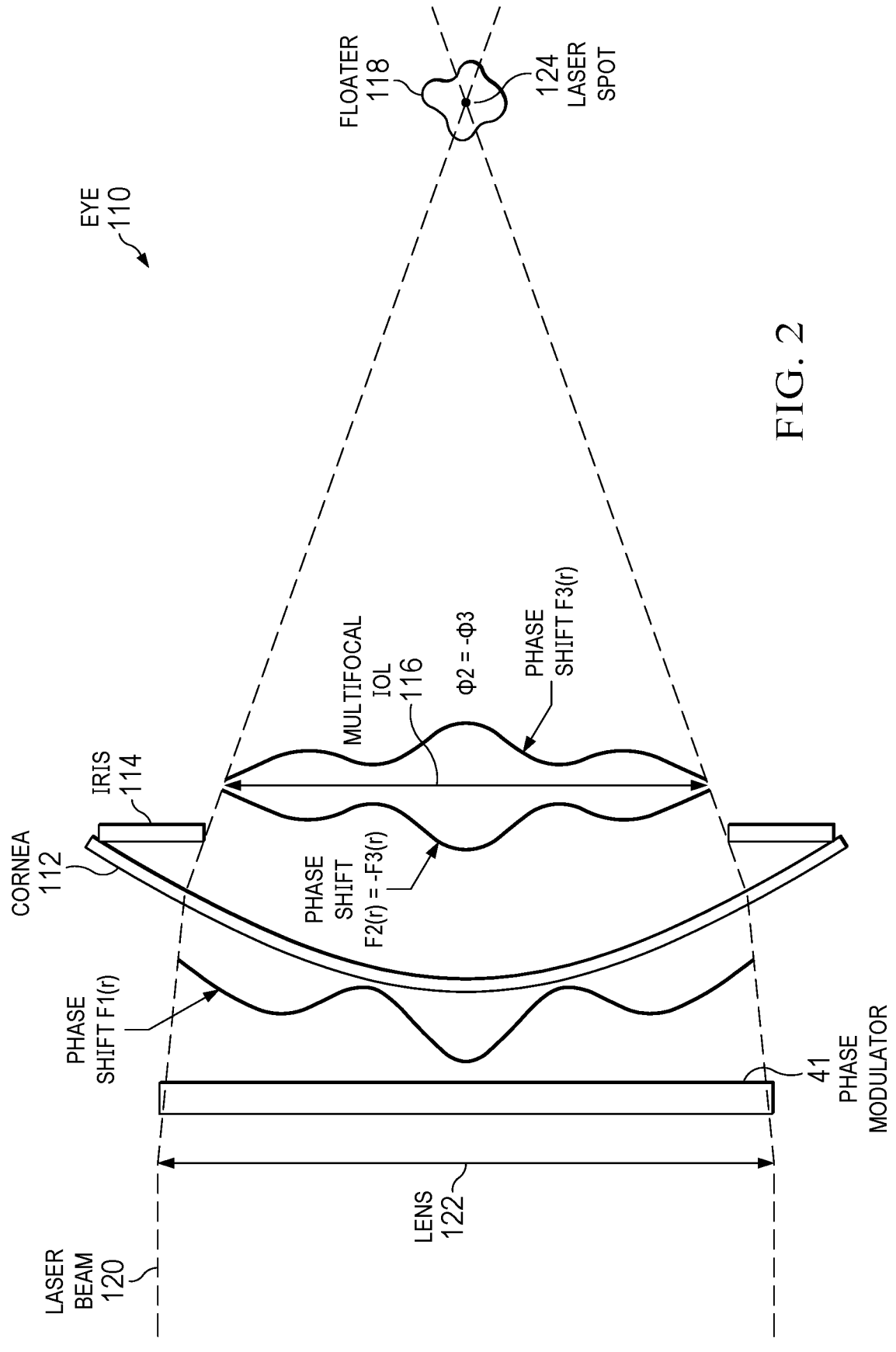
FIG. 2 illustrates an example of phase modulator that adds a phase shift to a laser beam 120 treating an eye, according to certain embodiments.

FIG. 2 illustrates an example of phase modulator 41 that adds a phase shift to a laser beam 120 treating an eye 110, according to certain embodiments. In the example, eye 110 includes a cornea 112, an iris 114, and a multifocal IOL 116. Multifocal IOL 116 is designed to add a phase shift F3($r$) to light entering eye 110. A floater 118 is in the vitreous of eye 110.

As an example of operation, laser beam 120 is directed towards eye 110. Lens 122 directs laser beam 120 towards phase modulator 41. Phase modulator 41 adds a phase profile F1($r$) to laser beam 120. Laser beam 120 enters eye 110, and the phase front F1($r$) changes to phase front F2($r$) when laser beam 120 reaches multifocal IOL 116. Phase front F2($r$) is the inverse of the phase shift F3 generated by the IOL. As the laser beam passes through the IOL, phase shift F3 compensates for the phase shift F2, such that the IOL behaves as a monofocal lens with only one focus at laser spot 124 at floater 118.

Figure 3:
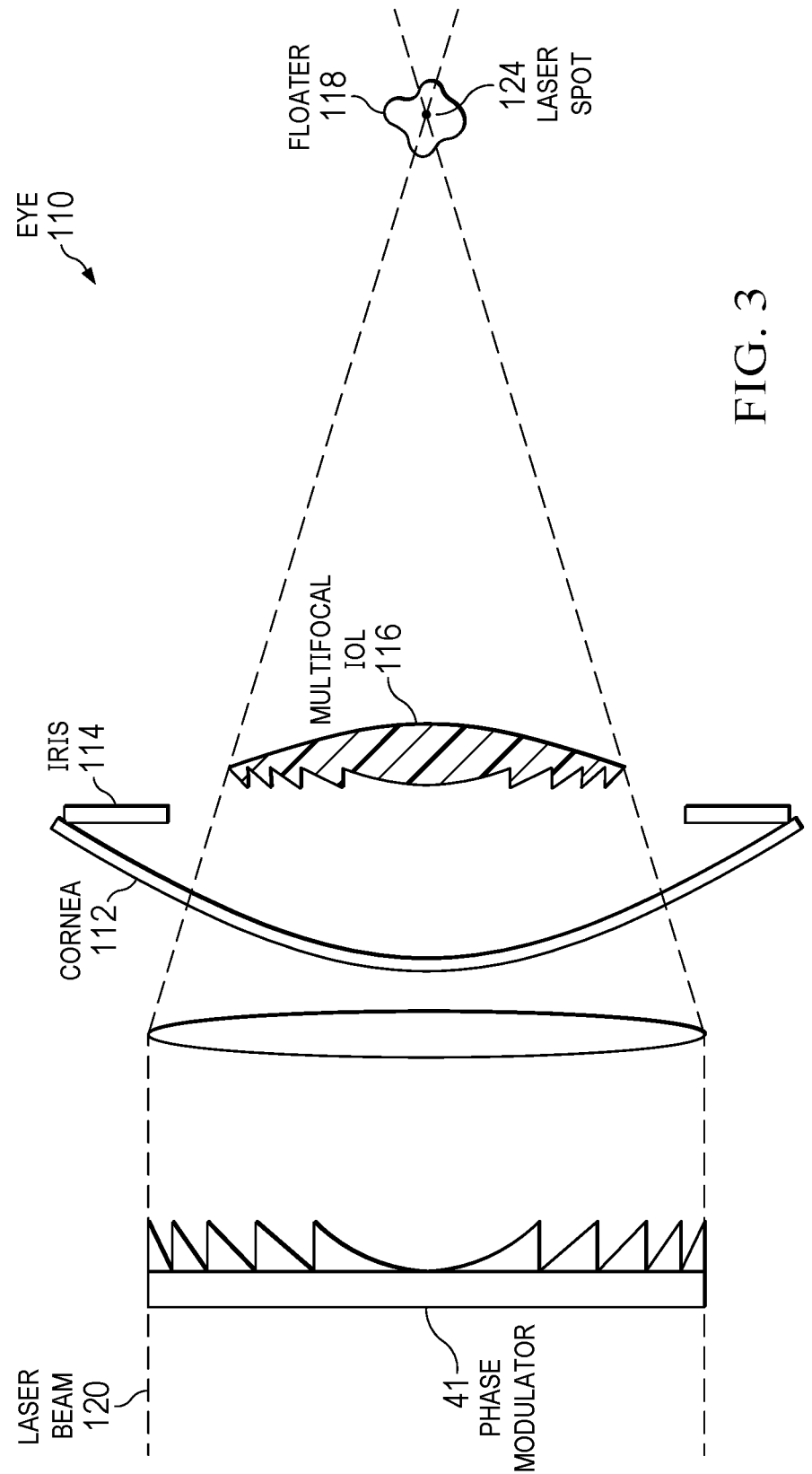
FIG. 3 illustrates an example of phase modulator that adds a phase shift to a laser beam 120 treating an eye, according to certain embodiments.

FIG. 3 illustrates another example of phase modulator 41 that adds a phase shift to laser beam 120 treating eye 110, according to certain embodiments. In the example, eye 110 includes cornea 112, iris 114, and multifocal IOL 116. Multifocal IOL 116 is designed to add a phase shift F3($r$) with, e.g., a +3-diopter power to light entering eye 110. Phase modulator 41 adds a phase profile F1($r$) to laser beam 120. Phase front F1($r$) changes to phase front F2($r$) when laser beam 120 reaches multifocal IOL 116. Phase front F2($r$) is the inverse of the phase shift F3($r$) generated by the IOL. As the laser beam passes through the IOL, phase shift F3($r$) compensates for the phase shift F2($r$), such that IOL 116 behaves as a monofocal lens with only one focus at laser spot 124 at floater 118.

A component (such as the control computer) of the systems and apparatuses disclosed herein may include an interface, logic, and/or memory, any of which may include computer hardware and/or software. An interface can receive input to the component and/or send output from the component, and is typically used to exchange information between, e.g., software, hardware, peripheral devices, users, and combinations of these. A user interface is a type of interface that a user can utilize to communicate with (e.g., send input to and/or receive output from) a computer. Examples of user interfaces include a display, Graphical User Interface (GUI), touchscreen, keyboard, mouse, gesture sensor, microphone, and speakers.

Logic can perform operations of the component. Logic may include one or more electronic devices that process data, e.g., execute instructions to generate output from input. Examples of such an electronic device include a computer, processor, microprocessor (e.g., a Central Processing Unit (CPU)), and computer chip. Logic may include computer software that encodes instructions capable of being executed by an electronic device to perform operations. Examples of computer software include a computer program, application, and operating system.

A memory can store information and may comprise tangible, computer-readable, and/or computer-executable storage medium. Examples of memory include computer memory (e.g., Random Access Memory (RAM) or Read Only Memory (ROM)), mass storage media (e.g., a hard disk), removable storage media (e.g., a Compact Disk (CD) or Digital Video or Versatile Disk (DVD)), database, network storage (e.g., a server), and/or other computer-readable media. Particular embodiments may be directed to memory encoded with computer software.

Although this disclosure has been described in terms of certain embodiments, modifications (such as changes, substitutions, additions, omissions, and/or other modifications) of the embodiments will be apparent to those skilled in the art. Accordingly, modifications may be made to the embodiments without departing from the scope of the invention. For example, modifications may be made to the systems and apparatuses disclosed herein. The components of the systems and apparatuses may be integrated or separated, or the operations of the systems and apparatuses may be performed by more, fewer, or other components, as apparent to those skilled in the art. As another example, modifications may be made to the methods disclosed herein. The methods may include more, fewer, or other steps, and the steps may be performed in any suitable order, as apparent to those skilled in the art.

To aid the Patent Office and readers in interpreting the claims, Applicants note that they do not intend any of the claims or claim elements to invoke 35 U.S.C. § 112(f), unless the words "means for" or "step for" are explicitly used in the particular claim. Use of any other term (e.g., "mechanism," "module," "device," "unit," "component," "element," "member," "apparatus," "machine," "system," "processor," or "controller") within a claim is understood by the applicants to refer to structures known to those skilled in the relevant art and is not intended to invoke 35 U.S.C. § 112(f).

What is claimed:

1. An ophthalmic laser system, comprising:
a laser device configured to direct a laser beam towards a target in an eye, an intraocular lens (IOL) disposed within the eye, the IOL having a phase profile configured to yield an IOL phase shift of light entering the eye, the laser device comprising:
a laser configured to generate the laser beam; and
a phase modulator having a phase front configured to yield a first phase shift of the laser beam that changes to a second phase shift when the laser beam reaches the IOL, the second phase shift being an inverse to the IOL phase shift; and
a computer configured to:
receive the IOL phase shift for the IOL; and
instruct the laser device to direct the laser beam towards the target.

2. The ophthalmic laser system of claim 1, the target comprising an eye floater.

3. The ophthalmic laser system of claim 1, the phase modulator comprising a diffractive optical element.

4. The ophthalmic laser system of claim 1, the phase modulator comprising a spatial light modulator.

5. The ophthalmic laser system of claim 4, the computer configured to program the spatial light modulator to yield the first phase shift.

6. The ophthalmic laser system of claim 1, the computer configured to:
calculate the second phase shift as an inverse of the IOL phase shift; and
calculate the first phase shift from the second phase shift.

7. The ophthalmic laser system of claim 6, the computer configured to determine the IOL phase shift by measuring a phase shift of the IOL.

8. The ophthalmic laser system of claim 6, the computer configured to calculate the first phase shift from the second phase shift by:

determining how the first phase shift changes between the phase modulator and the IOL according to wavefront propagation theory.

9. The ophthalmic laser system of claim 1, further comprising:

an ophthalmic microscope configured to gather light reflected from within the eye to yield an image of the eye.

10. The ophthalmic laser system of claim 9, the ophthalmic microscope comprising a slit lamp.

11. A method for performing laser vitreolysis, comprising:

receiving, by a computer, an intraocular lens (IOL) phase shift for an IOL;

instructing, by the computer, a laser device to direct a laser beam towards a target in an eye, the IOL disposed within the eye, the IOL having a phase profile configured to yield the IOL phase shift of light entering the eye, the laser device comprising a laser and a phase modulator, the phase modulator having a phase front configured to yield a first phase shift of the laser beam that changes to a second phase shift when the laser beam reaches the IOL, the second phase shift being an inverse to the IOL phase shift;

generating, by the laser, the laser beam;

modulating, by the phase modulator, the laser beam to yield the first phase shift of the laser beam; and directing, by the laser device, the laser beam towards the target in the eye.

12. The method of claim 11, the target comprising an eye floater.

13. The method of claim 11, the phase modulator comprising a diffractive optical element.

14. The method of claim 11, the phase modulator comprising a spatial light modulator.

15. The method of claim 14, further comprising:

programming, by the computer, the spatial light modulator to yield the first phase shift.

16. The method of claim 11, further comprising:

calculating, by the computer, the second phase shift as an inverse of the IOL phase shift; and calculating, by the computer, the first phase shift from the second phase shift.

17. The method of claim 16, further comprising:

determining, by the computer, the IOL phase shift by measuring a phase shift of the IOL.

18. The method of claim 16, further comprising:

calculating, by the computer, the first phase shift from the second phase shift by determining how the first phase shift changes between the phase modulator and the IOL according to wavefront propagation theory.

19. The method of claim 11, further comprising:

gathering, by an ophthalmic microscope, light reflected from within the eye to yield an image of the eye.

20. The method of claim 19, the ophthalmic microscope comprising a slit lamp.

* * * * *